United States Patent
Venkatesh et al.

(10) Patent No.: US 6,365,196 B1
(45) Date of Patent: Apr. 2, 2002

(54) CONTROLLED RELEASE SOLID DOSAGE FORMS OF LITHIUM CARBONATE

(75) Inventors: Gopadi M. Venkatesh, Blue Brook, OH (US); Nageswara R. Palepu, Broomfield, CO (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/509,880

(22) PCT Filed: Oct. 1, 1998

(86) PCT No.: PCT/US98/20579

§ 371 Date: May 18, 2000

§ 102(e) Date: May 18, 2000

(87) PCT Pub. No.: WO99/17751

PCT Pub. Date: Apr. 15, 1999

Related U.S. Application Data

(60) Provisional application No. 60/060,909, filed on Oct. 3, 1997.

(51) Int. Cl.$^7$ .............................................. A61K 33/00
(52) U.S. Cl. ...................................... 424/715; 424/715
(58) Field of Search ........................................ 424/715

(56) References Cited

U.S. PATENT DOCUMENTS

| 5,415,878 A | 5/1995 | Newton et al. | 424/722 |
|---|---|---|---|
| 5,690,959 A | 11/1997 | Palepu et al. | 424/472 |
| 5,824,344 A | 10/1998 | Palepu et al. | 424/489 |
| 5,827,537 A | 10/1998 | Palepu et al. | 424/472 |

FOREIGN PATENT DOCUMENTS

| GB | 2016922 | * | 9/1979 |
|---|---|---|---|
| GB | 2133285 | * | 7/1984 |

* cited by examiner

*Primary Examiner*—Sabiha Qazi
(74) *Attorney, Agent, or Firm*—Wayne J. Dustman; William T. King; Charles M. Kinzig

(57) ABSTRACT

A process for preparing controlled release solid dosage forms of lithium carbonate by using a dissolution rate stabilizer and a hydrophobic waxy material.

8 Claims, No Drawings

CONTROLLED RELEASE SOLID DOSAGE FORMS OF LITHIUM CARBONATE

This Appln is a 371 of PCT/US98/20579 filed Oct. 1, 1998, which claims benefit of Prov. No. 60/060,909 filed Oct. 3, 1997.

FIELD OF THE INVENTION

This invention relates to processes for preparing controlled release solid dosage forms of lithium carbonate ($Li_2CO_3$) for oral administration and controlled release solid dosage forms of lithium carbonate.

BACKGROUND OF THE INVENTION

Lithium carbonate is indicated in the treatment of manic episodes of manic-depressive illness and is commercially available in controlled release tablets under the tradename Eskalith CR®. In addition to the active ingredient—lithium carbonate, approx. 91%,—Eskalith CR® tablets contain alginic acid, 1%, gelatin, 4%, sodium starch glycolate, approx. 4%, iron oxide, trace amount, and magnesium stearate, 1%, as inactive ingredients. Eskalith CR® tablets have been manufactured for a number of years by a high shear wet granulation process that is characterized by a significant time dependent retardation in the dissolution rate of lithium carbonate which results in a shortened shelf-life for the product. Furthermore, significant batch to batch variability in the release rates of the active ingredient, both initially and on storage, is a persistent problem with the current process/product. The batch to batch variability in the release rate of lithium carbonate is of particular concern to the therapeutic use of this agent because lithium toxicity is closely related to serum lithium levels, and can occur at doses close to therapeutic levels. Lithium toxicity is so much of a concern that it is recommended that facilities for prompt and accurate serum lithium determinations be available before initiating therapy with lithium carbonate.

Thus, there is a need in the art for processes for preparing controlled release solid dosage forms of lithium carbonate and controlled release solid dosage forms of lithium carbonate which exhibit batch to batch consistency in release rates and stabilized dissolution profiles over time.

As disclosed herein, suitable controlled release solid dosage forms of lithium carbonate and processes for preparing the same have now been discovered

DETAILED DESCRIPTION OF THE INVENTION

All publications, including but not limited to patents and patent applications, cited in this specification are herein incorporated by reference as though fully set forth.

By the term "hydrophobic waxy material", "waxy material" or "wax" as used herein, is meant a fatty acid, alcohol or ester, alone or an admixture thereof. More specifically, the fatty acid may have from about 10 to about 22 carbon atoms and may be, for example, decanoic, stearic, palmitic, lauric or myristic acid.

The fatty alcohols may have from about 14 to about 31 carbon atoms and may be, for example, lauryl alcohol. cetyl, stearyl, myristyl, carbucyl or ceryl alcohol.

The esters may be mono-, di-, or triglyceryl esters. The hydrophobic waxy material may be modified by waxy materials of natural or synthetic sources. Exemplary of such waxes are beeswax, spermaceti wax or carnauba wax.

Preferred hydrophobic waxy materials for use herein include: cetyl alcohol, carnauba wax, glyceryl behenate (Compritol® from Gattefosse Corp.) glyceryl palmitostearate (Precirol® from Gattefosse Corp.) glyceryl monostearate and glyceryl distearate.

By the term "dissolution rate stabilizer" as used herein is meant organic acids such as fumaric acid, citric acid, tartaric acid, maleic acid, malic acid, ascorbic acid, succinic acid, sorbic acid and their anhydrides and salts. Poorly water soluble acids are preferred. Particularly preferred acids for use herein are fumaric acid and malic acid.

By the term "formulated into solid dosage forms" and derivatives thereof, as used herein preferably includes filling hard gelatin capsules and compressing into tablets.

By the term "thermal infusion" and derivatives thereof, as used herein is meant that the pharmaceutically active material—lithium carbonate—is blended with a hydrophobic waxy material and optional pharmaceutically acceptable excipient(s) and then optionally compacted, followed by dry granulation in a granulator at a suitable thermal infusion temperature and then optionally milled and screened to form thermal infusion granules.

When referring to thermally infusing blends in which the percentage of hydrophobic waxy material is about 30% by weight, preferably less than 20%, in relation to the pharmaceutically active material, the term "suitable thermal infusion temperature" or "thermal infusion temperature" and derivatives thereof, as used herein includes ambient temperature and temperatures above the extrapolated onset temperature, preferably less than 15° C. above the melting temperature, of the hydrophobic waxy material.

The "extrapolated onset temperature" represents that temperature corresponding to the intersection of the pre-transition baseline with the extrapolated leading edge of the endotherm (melting curve). For glyceryl behenate the extrapolated onset temperature is about 68° C.

Additional aspects relating to thermal infusion are found in International Publication Number WO 94/27557, having an International Publication Date of Dec. 8, 1994, the entire specification of which is hereby incorporated by reference.

The present invention relates to a process for preparing controlled release solid dosage forms of lithium carbonate ($Li_2CO_3$) which comprises blending lithium carbonate, a hydrophobic waxy material, preferably glyceryl behenate, a dissolution rate stabilizer, preferably fumaric acid, and optional pharmaceutically acceptable excipient(s), preferably microcrystalline cellulose, in a suitable mixer. The blend is converted into granules of desired particle size distribution by a dry granulating process which preferably consist of the steps of roller compacting, milling and screening. The granules thus prepared are formulated into solid dosage forms.

The order in which the indicated ingredients are utilized in the presently invented process is not critical. All orders of addition of the indicated ingredients are within the scope of the invention. However, the most advantageous process comprises blending lithium carbonate, in about 40 to 90% by weight preferably 65 to 85% most preferably 80 to 85%, a hydrophobic waxy material, preferably glyceryl behenate, in about 5 to 30% by weight preferably 5 to 25%, most preferably 8–23% in relation to the pharmaceutically active material, and optional, pharmaceutically acceptable excipient(s), preferably microcrystalline cellulose, in about 5 to 10% by weight, in a suitable mixer. The blend is converted into granules of desired particle size distribution by a dry granulating process which preferably consist of the steps of roller compacting, milling and screening. The granules thus prepared are blended with a dissolution rate stabilizer, preferably fumaric acid, in an amount greater than 1% to about 15% by weight, preferably 3 to 15%, most preferably about 6 to 13%, and a pharmaceutically acceptable excipient, preferably microcrystalline cellulose, in about 5 to 30% by weight, preferably 10 to 25%, most preferably 10 to 20%. in a suitable mixer and formulated into solid dosage forms.

In noting the percentages of the ingredients above and throughout the specification and the claims, the wax content as well as the other excipients are always stated in relation to the active material (for example, 85/15 means 85 parts of lithium carbonate blended with 15 parts of an excipient such as glyceryl behenate or 80/15/5 means 80 parts of lithium carbonate, 15 parts of an excipient such as glyceryl behenate and 5 parts of an excipient such as microcrystalline cellulose).

An alternative step in the presently invented process involves subjection of a blend, prepared as described herein, to thermal infusion prior to or during the dry granulating process.

The ability of the presently invented process to prepare the presently invented controlled release solid dosage forms of lithium carbonate, which exhibit batch to batch consistency in release rates and stabilized dissolution profiles over time, is primarily attributed to the addition of a dissolution rate stabilizer to the formulation and using a dry granulating process instead of a wet granulating process as was previously used.

Additional pharmaceutically acceptable excipients which are contemplated for use in the process and compositions of the present invention include release rate modulating polymers, such as high molecular weight poly(ethylene oxide) (available under the name Polyox WSR of Union Carbide Corporation), lactose, polyvinylpyrrolidone and pharmaceutically acceptable coloring agents.

In a general procedure for the processes of the current invention, lithium carbonate, a hydrophobic waxy material and optional pharmaceutical excipients are blended in a suitable mixer and granules of desired particle size distributions are manufactured in a dry granulating process, preferably by slugging or compacting, milling and screening. The granules may be produced using a continuous process or a batch process. Granules of desired mesh size (such as <#18 & >#80 mesh. i.e., passing through #18 mesh sieve but retained on #80 mesh sieve) are prepared, optionally by subjecting a blend, prepared as described herein, to thermal infusion prior to or during the dry granulating process.

The granules thus prepared are blended with optional pharmaceutical excipients and a dissolution rate stabilizer, preferably an organic acid such as fumaric acid, and filled into hard gelatin capsules or compressed into tablets. In another variation of the process, the powdered blend is granulated by melt granulation instead of by roller compaction. This melt granulation is milled to produce granules with a desired particle size distribution. These granules are blended with optional pharmaceutical excipients and a dissolution rate stabilizer, preferably an organic acid, and filled into hard gelatin capsules or compressed into tablets.

By the term "pharmaceutically acceptable excipients" as used herein is meant additives such as diluents, fillers, and binders which are optionally utilized in accordance with the process of the present invention. The excipients commonly used in pharmaceutical industry are well described in literature such as described in *Handbook of Pharmaceutical Excipients*, A. Wade and P. J. Weller (Editors), American Pharmaceutical Association (1994). Pharmaceutically acceptable fillers and diluents include but are not limited to lactose (hydrous as well as anhydrous), starch [unmodified (corn starch) or modified (for e.g., Starch 1500 available from Colorcon)], mannitol, sorbitol, cellulose, inorganic sulfates and phosphates. Pharmaceutically acceptable binders include but are not limited to gelatin, corn starch, modified starch (Starch 1551, pregelatinized starch). hydroxypropyl methyl cellulose (HPMC) and hydroxypropyl cellulose(HPC). Examples of excipients suitable for modified release applications in accordance with the present invention include but are not limited to) waxy materials such as glyceryl behenate (Compritol®), glyceryl palmitostearate (Precirol®), saturated polyglycolyzed glycerides (Gelucire®) [all from Gattefosse s.a., France], carnauba wax and a series of high molecular weight non-ionic water-soluble high molecular weight poly(ethylene oxide) polymers (Polyoxe® WSR, Union Carbide Corp.).

The present invention also relates to novel compositions of lithium carbonate prepared by the dry granulating process described above. The presently invented compositions of lithium carbonate comprise lithium carbonate, a hydrophobic waxy material, preferably glyceryl behenate, a dissolution rate stabilizer, preferably fumaric acid, and optional pharmaceutically acceptable excipient(s), preferably microcrystalline cellulose.

The presently invented compositions of lithium carbonate suitably comprise lithium carbonate, in about 40 to 90% by weight preferably 65 to 85% most preferably 80 to 85%, a hydrophobic waxy material, preferably glyceryl behenate, in about 5 to 30% by weight preferably 5 to 25%, most preferably 8–23% in relation to the pharmaceutically active material, pharmaceutically acceptable excipient(s), preferably microcrystalline cellulose (added extragranularly or both intra- and extra-granularly), in about 5 to 30% by weight, preferably 10 to 25%, most preferably 15 to 25%, and a dissolution rate stabilizer, preferably fumaric acid in an amount greater than 1% to about 15% by weight, preferably 3 to 15%, most preferably 6 to 13%.

A further contemplated aspect of the presently invented process and compositions relates to subsequently coating the prepared compositions with a moisture barrier or controlled release polymer coating.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLES OF FORMULATIONS

Example 1

Lithium carbonate USP by itself (batchsize: 2 kgs) was roller compacted at 750–800 PSI using a Fitzpatrick roller compactor, milled using a Fitzmill using a perforated screen and sifted to produce #18–40 mesh granules [the sieve fraction passing through #18 mesh screen but collected on the #80 mesh screen]. 450 mg lithium carbonate tablets weighing 584 mg (77% granules blended with 22.5% microcrystalline cellulose and 0.5% magnesium stearate) were manufactured from these granules using a Stokes tablet press. (Formula A Tablets).

Example 2

A blend containing 87.3% lithium carbonate, 0.2% iron oxide, 7.5% glyceryl behenate and 5.0% microcrystalline cellulose [batchsize: 50 kgs] was roller compacted using a Fitzpatrick L-83 chilsonator, milled and sifted. 15 kgs of #18–40 mesh granules were heat treated in a fluid bed granulator [Glatt GPCG-UD30H] at 64±2.0° C. for 15 min. 12.0 kgs of the heat treated granules were blended with 2.925 kgs of microcrystalline cellulose and 0.075 kg magnesium stearate using a bin blender and compressed into 450 mg lithium carbonate tablets [tablet weight: 644 mg (Formula B Tablets)] using a Hata tablet press.

Example 3

95 kgs lithium carbonate and 5 kgs Compritol were blended in a 10 cu.ft. V-blender. #18–40 mesh size dry granules were manufactured using a continuous cycle Fitzpatrick 4L×10D chilsonator system. In this continuous cycle system, the material is roller compacted. milled and sifted into three fractions—oversize (>#18 mesh) granules, #18–40 mesh granules and fines (<#40 mesh); the oversize granules and fines are blended with virgin material, and the process continues. 7.4 kgs of #18–40 mesh granules were blended with 2.55 kg microcrystalline cellulose and 0.05 kg magnesium stearate and compressed into 450 mg tablets (tablet weight: 640.1 mg [Formula C Tablets]). 7.4 kgs of #18–40 mesh granules were blended with 2.05 kg of microcrystalline cellulose, 0.5 kg tartaric acid and 0.05 kg magnesium stearate and compressed into 450 mg lithium carbonate tablets [tablet weight: 640.1 mg (Formula D Tablets)]. 7.4 kgs of #18–40 mesh granules were blended with 2.05 kgs of microcrystalline cellulose, 0.5 kg fumaric acid and 0.05 kg magnesium stearate and compressed into 450 mg tablets [tablet weight: 644.1 mg (Formula E Tablets)]. 7.4 kgs of #18–40 mesh granules were blended with 2.175 kgs of microcrystalline cellulose, 0.375 kg fumaric acid and 0.05 kg magnesium stearate and compressed into 450 mg tablets [tablet weight: 644.1 mg (Formula F Tablets)].

Example 4

A blend [batchsize: 67.0 kgs] containing 79.8% lithium carbonate, 0.2% iron oxide pigment (Cosmetic Ochre) and 20% Compritol is roller compacted, milled and sifted. 53.07 kgs of #18–40 mesh granules were blended with 9.63 kgs of microcrystalline cellulose, 4.0 gks of fumaric acid and 300.0 gm magnesium stearate and compressed into 450 mg tablets [tablet weight: 670 mg (Formula G Tablets)].

Example 5

A blend [batchsize: 20 kgs] containing 84.8% lithium carbonate, 0.2% an iron oxide pigment and 15% Compritol was roller compacted, milled and sifted. 1061.4 gms of #30–80 granules were blended with 192.6 gm microcrystalline cellulose, 80.0 gm fumaric acid and 6.0 gm magnesium stearate and compressed into 450 mg, tablets [tablet weight: 670.0 mg (Formula H Tablets)]. A mixture of 849.0 gm #30–80 granules and 212.2 gm #80–140 mesh granules [i.e., 80% of #30–80 and 20% of #80–140 mesh granules] was used in place of the #30–80 mesh granules in Formula H Tablets above to produce 450 mg tablets [batchsize: 1340 gms; (Formula I Tablets)]. 1061.4 gm granules passing through a #30 mesh screen were used in place of the #30–80 mesh granules in Formula H Tablets above to produce 450 mg tablets [batchsize: 1340 gms; (Formula J Tablets)].

Example 6

A blend [batchsize: 30 kgs] containing 82.3% lithium carbonate, 0.2% an iron oxide pigment, 12.5% Compritol and 5.0% microcrystalline cellulose was roller compacted, milled and sifted. 16824.6 gms of #30–140 granules were blended with 1852.4 gm microcrystalline cellulose, 1230.8 gm fumaric acid and 92.4 gm magnesium stearate and compressed into 450 mg tablets [tablet weight: 650.0 mg (Formula K Tablets)].

Dissolution Testing

The 450 mg lithium carbonate tablets of Examples 1 to 3 were initially tested in purified water at 37° C. using USP Apparatus 1 (Basket@ 100 rpm). The percentage release in relation to the USP reference material was determined as a function of time using an atomic absorption spectrophotometer or an inductively coupled plasma emission sphectrometer. The tablets of Examples 4 and 5 were tested in 0.1N HCl containing 0.05% SDS using USP Apparatus 1 (Baskets@ 100 rpm) while the tablets of Example 6 were tested in 0.1N HCl containing 0.05% SDS using USP Apparatus 1 (Baskets@ 50 rpm).

Dissolution Profiles from Tablets on Stability

TABLE 1

Dissolution Data for Lithium Carbonate Prototype Formulas

| Conditions | % Release | | |
|---|---|---|---|
| | 1 Hour | 3 Hours | 7 Hours |
| Formula A | | | |
| Initial | 84 | 99 | |
| 40° C./75% RH, 1 mo | 33 | 77 | 96 |
| Formula B | | | |
| Initial | 27 | 47 | 63 |
| Ambient, 7 mo | 18 | 38 | 59 |
| 30° C., 1 mo | 26 | 47 | 64 |
| 30° C./75% RH, 1 mo | 26 | 45 | 62 |
| 30° C./75% RH, 3 mo | 15 | 31 | 46 |
| 30° C./75% RH, 6 mo | 13 | 29 | 44 |
| 40° C., 1 mo | 21 | 40 | 56 |
| 40° C./75% RH, 1 mo | 16 | 32 | 47 |

The data represented in Table 1 shows that tablets of Formula A released the drug rapidly while tablets of Formula B released steadily for over 7 hours. However, the storage of tablets both formulas in sealed high density ploy(ethylene) bottles at accelerated temperatures, such as 40° C./75% RH, resulted in a significant retardation in dissolution. Formula B tablets stored at 30° C./75% RH for 6 months also showed significant drops in release rates.

TABLE 2

Dissolution Profiles of Lithium Carbonate Formulations on Stability

| Formula | Condition | % Release | | | |
|---|---|---|---|---|---|
| | | 1 hr | 3 hr | 7 hr | 12 hr |
| Formula C | No Acid | | | | |
| | Initial | 37 | 62 | 82 | 92 |
| | 40° C./75% RH 2 wks | 19 | 40 | 59 | 72 |
| Formula D | 5.0% Tartaric Acid | | | | |
| | Initial | 40 | 67 | 89 | 98 |
| | 25° C./60% RH 2 mo | 47 | 78 | 95 | 97 |
| | 40° C./75% RH 1 mo | 35 | 67 | 91 | 100 |
| | 40° C./75% RH 2 mo | 12 | 28 | 46 | 60 |
| Formula E | 5.0% Fumaric Acid | | | | |
| | Initial | 33 | 57 | 76 | 87 |

TABLE 2-continued

Dissolution Profiles of Lithium Carbonate Formulations on Stability

| Formula | Condition | % Release | | | |
|---|---|---|---|---|---|
| | | 1 hr | 3 hr | 7 hr | 12 hr |
| | 40° C./75% RH 2 wks | 28 | 56 | 82 | 94 |
| | 40° C./75% RH 5 wks | 21 | 52 | 81 | 93 |
| | 40° C./75% 2 mo | 21 | 55 | 84 | 97 |
| | 40° C./75% RH 3.5 mo | 19 | 51 | 79 | 92 |
| Formula F | 3.75% Fumaric Acid | | | | |
| | Initial | 37 | 66 | 89 | 98 |
| | 30° C./60% RH 6 wks | 29 | 56 | 79 | 92 |
| | Open 40° C./75% RH 5 wks | 13 | 32 | 54 | 70 |

The data represented in Table 2 presents drug release profiles from controlled release tablets of lithium carbonate prepared as described in Example 3. The data in this table indicates that incorporating an organic acid in a tablet formulation of lithium carbonate, such as tartaric acid or fumaric acid of the present invention, stabilizes the dissolution profile over time [by retarding the slowing down in dissolution]. The duration of stabilization has been shown to depend on the temperature of storage, the lower the temperature of storage, the longer the duration of dissolution stabilization that could be achieved. Also. highly water soluble acids such as citric and tartaric acids, appear to provide stabilization for shorter durations than the poorly water soluble fumaric acid [solubility of citric or tartaric acid in water is about a gram per ml. while that of fumaric acid is 6 mg per ml.]. The dissolution data on multiple batches of Formula E suggested that batch to batch consistency in release rates.

TABLE 3

Dissolution Data for Lithium Carbonate Controlled Release Formulas

| | % Release | | |
|---|---|---|---|
| | 1 hr | 3 hr | 7 hr |
| Formula G | | | |
| Initial | 22 | 51 | 84 |
| 30° C./60% RH, 3 mo | 21 | 54 | 90 |
| 40° C./75% RH, 3 mo | 16 | 40 | 75 |
| Formula H | | | |
| Initial | 26 | 56 | 86 |
| 30° C./60% RH, 3 mo | 25 | 53 | 84 |
| 40° C./75% RH, 3 mo | 21 | 52 | 81 |
| Formula I | | | |
| Initial | 22 | 51 | 88 |
| 30° C./60% RH, 1 mo | 21 | 52 | 82 |
| 40° C./75% RH, 1 mo | 19 | 45 | 83 |
| 30° C./60% RH, 6 mo | 20 | 50 | 91 |
| Formula J | | | |
| Initial | 23 | 58 | 94 |
| 25° C./60% RH, 6 mo | 21 | 49 | 89 |
| 25° C./60% RH, 12 mo | 20 | 46 | 81 |
| 30° C./60% RH, 3 o | 18 | 45 | 86 |
| 30° C./60% RH, 6 mo | 20 | 45 | 83 |
| 30° C./60% RH, 12 mo | 20 | 47 | 87 |
| 40° C./75% RH, 1 mo | 17 | 44 | 87 |
| 40° C./75% RH, 6 mo | 19 | 46 | 93 |
| Formula K | | | |
| Initial | 22 | 52 | 85 |

The data represented in Table 3 presents drug release profiles from controlled release tablets of lithium carbonate prepared as described in Examples 4 and 5. The data in this table indicates that incorporating fumaric acid in a tablet formulation of lithium carbonate, effectively stabilizes in-vitro release profiles from the tablets over time and provides for batch to batch consistency in release rates.

The above Examples demonstrate the ability of the presently invented process to prepare controlled release solid dosage forms of lithium carbonate and the ability of the presently invented controlled release solid dosage forms of lithium carbonate to exhibit batch to batch consistency in release rates and stabilized dissolution profiles over time.

While the preferred embodiments of the invention are illustrated by the above, it is to be understood that the invention is not limited to the precise instructions herein disclosed and that the right to all modifications coming within the scope of the following claims is reserved.

What is claimed is:

1. A process for preparing controlled release solid dosage forms of lithium carbonate which comprises the steps of:

(a) blending lithium carbonate, a hydrophobic waxy material, a dissolution rate stabilizer and optional pharmaceutical excipients; and (b) formulating the resulting blend into solid dosage forms.

2. The process of claim 1 which comprises the steps of:

(a) blending lithium carbonate, a hydrophobic waxy material, a dissolution rate stabilizer and optional pharmaceutical excipients;

(b) dry granulating the resulting blend into granules; and (c) formulating the resulting granules into solid dosage forms.

3. The process of claim 2 which comprises the steps of:

(a) blending lithium carbonate, a hydrophobic waxy material and optional pharmaceutical excipients;

(b) dry granulating the resulting blend into granules;

(c) blending the resulting granules with optional pharmaceutical excipients and a dissolution rate stabilizer, and (c) formulating the resulting blend into solid dosage forms.

4. The process of claim 3 which comprises the steps of:

(a) blending lithium carbonate a hydrophobic waxy material and optional pharmaceutically acceptable excipients;

(b) roller compacting, milling and sieving the resulting blend to produce granules of a desired particle size distribution;

(c) preparing a compression mix by blending said granules with optional pharmaceutically acceptable excipients and a dissolution rate stabilizer; and (d) filling said compression mix into hard gelatin capsules or compressing into tablets.

5. The process of claim 4 which comprises:

(a) subjecting lithium carbonate granules prepared as in claim 4, step (a) to thermal infusion;

(b) preparing a compression mix by blending said granules with optional pharmaceutically acceptable excipients and a dissolution rate stabilizer; and (c) filling said compression mix into hard gelatin capsules or compressing into tablets.

6. The process according to claim 1 wherein the dissolution rate stabilizer is selected form tartaric acid, citric acid, fumaric acid, ascorbic acid, succinic acid, maleic acid, malic acid or sorbic acid or any pharmaceutically acceptable organic acid anhydride or salt thereof.

7. Controlled release solid dosage forms of lithium carbonate prepared according claim 1.

8. A controlled release solid dosage form of lithium carbonate containing:

(a) about 40 to 90% by weight lithium carbonate;
(b) a hydrophobic waxy material in about 5 to 30% by weight;
(c) a dissolution rate stabilizer in an amount greater than 1% to about 15% by weight; and
(d) optional pharmaceutically acceptable excipients.

\* \* \* \* \*